United States Patent
Schindler et al.

(10) Patent No.: US 7,518,024 B2
(45) Date of Patent: *Apr. 14, 2009

(54) PROCESS FOR PREPARING 1-BUTENE

(75) Inventors: Götz-Peter Schindler, Mannheim (DE);
Andreas Brodhagen, Dannstadt-Schauernheim (DE);
Thorsten Johann, Limburgerhof (DE);
Thomas Hill, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 112 days.

This patent is subject to a terminal disclaimer.

(21) Appl. No.: 10/577,198

(22) PCT Filed: Oct. 27, 2004

(86) PCT No.: PCT/EP2004/012139

§ 371 (c)(1),
(2), (4) Date: May 17, 2006

(87) PCT Pub. No.: WO2005/042450

PCT Pub. Date: May 12, 2005

(65) Prior Publication Data

US 2007/0161841 A1    Jul. 12, 2007

(30) Foreign Application Priority Data

Oct. 27, 2003    (DE)    ............... 103 50 045

(51) Int. Cl.
*C07C 5/327*    (2006.01)
*C07C 5/32*    (2006.01)

(52) U.S. Cl. .............. 585/325; 585/616; 585/621; 585/628

(58) Field of Classification Search .......... 585/325, 585/616, 621, 628, 629
See application file for complete search history.

(56) References Cited

U.S. PATENT DOCUMENTS

| | | | |
|---|---|---|---|
| 3,161,670 A | 12/1964 | Adams et al. | |
| 4,408,085 A | 10/1983 | Gottlieb et al. | |
| 4,558,168 A | 12/1985 | Gussow et al. | |
| 4,718,986 A | 1/1988 | Comiotto et al. | |
| 4,788,371 A | 11/1988 | Imai et al. | |
| 4,902,849 A | 2/1990 | McKay et al. | |
| 4,996,387 A | 2/1991 | Gerhold et al. | |
| 4,996,849 A | 3/1991 | Burst et al. | |
| 5,087,780 A | 2/1992 | Arganbright | |
| 5,220,091 A | 6/1993 | Brinkmeyer et al. | |
| 5,389,342 A | 2/1995 | Savage et al. | |
| 5,430,220 A | 7/1995 | Khare et al. | |
| 5,877,369 A | 3/1999 | Wu et al. | |
| 5,955,640 A | 9/1999 | Paludetto et al. | |
| 6,414,209 B1 | 7/2002 | Herskowitz et al. | |
| 6,437,206 B1 | 8/2002 | Meyer et al. | |
| 6,670,303 B1 | 12/2003 | Heineke et al. | |
| 7,034,195 B2 | 4/2006 | Schindler et al. | |
| 2003/0220530 A1 | 11/2003 | Boelt et al. | |
| 2005/0119515 A1 | 6/2005 | Machhammer et al. | |
| 2005/0171311 A1 | 8/2005 | Schindler et al. | |

FOREIGN PATENT DOCUMENTS

| | | |
|---|---|---|
| DE | 199 37 105 | 2/2001 |
| DE | 199 37 106 | 2/2001 |
| DE | 199 37 107 | 2/2001 |
| DE | 102 11 275 | 9/2003 |
| EP | 0 117 146 | 8/1984 |
| EP | 0 129 900 | 1/1985 |
| EP | 0 705 136 | 4/1996 |
| EP | 0 751 106 | 1/1997 |
| EP | 0 992 284 | 4/2000 |
| GB | 628 686 | 9/1949 |
| GB | 2 018 815 | 10/1979 |
| WO | WO-99/29420 | 6/1999 |
| WO | WO-99/46039 | 9/1999 |
| WO | WO-2004/007408 | 1/2004 |
| WO | WO-2005/063656 | 7/2005 |

OTHER PUBLICATIONS

Sannfilippo, et al. "Fluidized Bed Reactors For Parraffins Dehydrogenation", Chemical Engineering Science, vol. 47, No. 9-11, pp. 2313-2318, 1992.

*Primary Examiner*—Thuan Dinh Dang
(74) *Attorney, Agent, or Firm*—Connolly Bove Lodge & Hutz LLP

(57) ABSTRACT

A process for preparing 1-butene from 1-butane, which includes providing a n-butane-containing feed gas stream; introducing of the n-butane-containing feed gas stream into at least one dehydrogenation zone and nonoxidative catalytic dehydrogenation of n-butane; removing hydrogen, the low-boiling secondary constituents and optionally water vapor to give a $C_4$ product gas stream containing 10-80% by volume of n-butane, 5-40% by volume of 1-butene, 10-50% by volume of 2-butene, 0-40% by volume of butadiene and 0-10% by volume of further gas constituents; introducing the $C_4$ product gas stream containing 10-80% by volume of n-butane, 10-60% by volume of 1-butene, 15-60% by volume of 2-butene, 0-5% by volume of butadiene and 0-10% by volume of further gas constituents, into a selective hydrogenation zone and selective hydrogenation of butadiene to 1- and/or 2-butene to give stream consisting essentially of n-butane, 1-butene and 2-butene; and separating of the stream distillation into a desired product.

12 Claims, No Drawings

PROCESS FOR PREPARING 1-BUTENE

RELATED APPLICATIONS

This application is a national stage application (under 35 U.S.C. 371) of PCT/EP2004/012139 filed Oct. 27, 2004 which claims benefit to German application 103 50 045.6 filed Oct. 27, 2003.

The invention relates to a process for preparing 1-butene.

Butenes can be prepared by thermal dissociation (steam cracking) of saturated hydrocarbons, customarily using naphtha as raw material. Steam cracking of naphtha produces a hydrocarbon mixture comprising methane, ethane, ethene, acetylene, propane, propene, propyne, allene, butenes, butadiene, butynes, methylallene, $C_5$-hydrocarbons and higher hydrocarbons.

A disadvantage of the production of butene by cracking is that relatively large amounts of ethene or propene are inevitably formed as coproducts.

As an alternative, butenes can be prepared from n-butane by catalytic dehydrogenation. However, this process has the disadvantage that the catalytic hydrogenation of n-butane forms 2-butene and butadiene in relatively large amounts in addition to 1-butene.

It is an object of the invention to provide a process for preparing 1-butene from 1-butane, in which coproducts are formed to a very small extent.

This object is achieved by a process for preparing 1-butene from 1-butane, which comprises the steps A) provision of an n-butane-containing feed gas stream a;
B) introduction of the n-butane-containing feed gas stream a into at least one dehydrogenation zone and nonoxidative catalytic dehydrogenation of n-butane to give a product gas stream b comprising n-butane, 1-butene, 2-butene, butadiene, low-boiling secondary constituents, hydrogen and possibly water vapor;
C) removal of hydrogen, the low-boiling secondary constituents and, if appropriate, water vapor to give a $C_4$ product gas stream c consisting essentially of n-butane, 1-butene, 2-butene and butadiene;
D) introduction of the $C_4$ product gas stream c consisting essentially of n-butane, 1-butene, 2-butene and butadiene into a selective hydrogenation zone and selective hydrogenation of butadiene to 1- and/or 2-butene to give a stream d consisting essentially of n-butane, 1-butene and 2-butene;
E) separation of the stream d into a stream e1 consisting essentially of 1-butene and a recycle stream e2 consisting essentially of 2-butene and n-butane and recirculation of the recycle stream e2 consisting essentially of 2-butene and n-butane to the dehydrogenation zone.

The process of the invention makes particularly effective use of the raw materials. Thus, losses of the raw material n-butane are minimized by recirculation of unreacted n-butane to the dehydrogenation. n-Butane is virtually completely reacted in this way. Butadiene formed in the dehydrogenation is converted into further product of value by selective hydrogenation, and 2-butene formed in the dehydrogenation or the selective hydrogenation is recirculated to the dehydrogenation. Thus, neither butadiene nor 2-butene is obtained as coproduct. Furthermore, the formation of ethene and propene is minimized compared to steam cracking as a result of the higher selectivity of the nonoxidative butane dehydrogenation.

In a first part A of the process, an n-butane-containing feed gas stream a is provided. n-Butane-rich gas mixtures such as liquefied petroleum gas (LPG) are usually used as raw material for this purpose. LPG consists essentially of $C_2$-$C_5$-hydrocarbons. In addition, it contains traces of methane and $C_6^+$-hydrocarbons. The composition of LPG can fluctuate widely. The LPG used advantageously contains at least 10% by weight of butanes.

As an alternative, an upgraded $C_4$-hydrocarbon stream from crackers or refineries can be used as feed gas stream a.

In a variant of the process of the invention, the provision of the n-butane-containing dehydrogenation feed gas stream comprises the steps A1) provision of a liquefied petroleum gas (LPG) stream,
A2) removal of propane and, if appropriate, methane, ethane and $C_5^+$-hydrocarbons (mainly pentanes, and also hexanes, heptanes, benzene and toluene) from the LPG stream to give a stream comprising butanes (n-butane and isobutane),
A3) removal of isobutane from the stream comprising butanes to give the n-butane-containing feed gas stream and, if appropriate, isomerization of the isobutane which has been separated off to form an n-butane/isobutane mixture and recirculation of the n-butane/isobutane mixture to the isobutane removal.

The removal of propane and, if appropriate, methane, ethane and $C_5^+$-hydrocarbons is carried out, for example, in one or more customary rectification columns. For example, low boilers (methane, ethane, propane) can be separated off overhead in a first column and high boilers ($C_5^+$-hydrocarbons) can be separated off at the bottom of a second column. This gives a stream comprising butanes (n-butane and isobutane) from which the isobutane is removed, for example, in a customary rectification column. The remaining, n-butane-containing stream is used as feed gas stream for the subsequent butane dehydrogenation.

The isobutane stream which has been separated off is preferably subjected to an isomerization. For this purpose, the isobutane-containing stream is fed into an isomerization reactor. The isomerization of isobutane to n-butane can be carried out as described in GB-A 2 018 815. This gives an n-butane/isobutane mixture which is fed into the n-butane/isobutane separation column.

The isobutane stream which has been separated off can also be passed to a further use, for example for preparing methacrylic acid, polyisobutene and methyl tert-butyl ether.

In a part B of the process, the n-butane-containing feed gas stream is fed into a dehydrogenation zone and subjected to a nonoxidative catalytic dehydrogenation. Here, n-butane is partially dehydrogenated over a dehydrogenation-active catalyst in a dehydrogenation reactor to form 1-butene and 2-butene, with butadiene also being formed. In addition, hydrogen and small amounts of methane, ethane, ethene, propane and propene are also obtained. Depending on the way in which the dehydrogenation is carried out, carbon oxides (CO, $CO_2$), water and nitrogen can also be present in the product gas mixture from the nonoxidative catalytic n-butane dehydrogenation. In addition, unreacted n-butane is present in the product gas mixture.

The nonoxidative catalytic n-butane dehydrogenation can be carried out with or without an oxygen-containing gas as cofeed.

A feature of the nonoxidative mode of operation compared to an oxidative mode of operation is the presence of hydrogen in the output gas. In oxidative dehydrogenation, free hydrogen is not formed in significant amounts.

The nonoxidative catalytic n-butane dehydrogenation can in principle be carried out in all reactor types and by all methods known from the prior art. A comparatively comprehensive description of dehydrogenation processes which are suitable for the purposes of the invention may be found in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable type of reactor is a fixed-bed tube reactor or a shell-and-tube reactor. In these, the catalyst (dehydrogenation catalyst and, when oxygen is employed as cofeed, optionally a specific oxidation catalyst) is present as a fixed bed in a reaction tube or in a bundle of reaction tubes. The reaction tubes are usually heated indirectly by a gas, e.g. a hydrocarbon such as methane, being burned in the space surrounding the reaction tubes. It is advantageous to apply this indirect form of heating only to the first about 20-30% of the length of the fixed bed and to heat the remaining length of the bed to the required reaction temperature by the radiant heat given off from the indirect heating. Customary internal diameters of the reaction tubes are from about 10 to 15 cm. A typical shell-and-tube reactor for dehydrogenation has from about 300 to 1000 reaction tubes. The temperature in the interior of the reaction tubes is usually in the range from 300 to 1200° C., preferably in the range from 500 to 1000° C. The working pressure is usually from 0.5 to 8 bar, frequently from 1 to 2 bar when using a low level of steam dilution (as in the Linde process for the dehydrogenation of propane) but can also be in the range from 3 to 8 bar when using a high level of steam dilution (as in the Phillips Petroleum Company's "steam active reforming process" (STAR process) for the dehydrogenation of propane or butane, cf. U.S. Pat. No. 4,902,849, U.S. Pat. No. 4,996,387 and U.S. Pat. No. 5,389,342). Typical GHSVs over the catalyst are from 500 to 2000 $h^{-1}$, based on hydrocarbon used. The catalyst geometry can, for example, be spherical or cylindrical (hollow or solid).

The nonoxidative catalytic n-butane dehydrogenation can also be carried out over a heterogeneous catalyst in a fluidized bed, as described in Chem. Eng. Sci. 1992 b, 47 (9-11) 2313. It is advantageous for two fluidized beds to be operated side by side, with one of these generally being regenerated at any given time. The working pressure is typically from 1 to 2 bar, and the dehydrogenation temperature is generally from 550 to 600° C. The heat required for the dehydrogenation is introduced into the reaction system by the dehydrogenation catalyst being preheated to the reaction temperature. When an oxygen-containing cofeed is mixed in, the preheaters can be omitted and the heat required can be generated directly in the reactor system by combustion of hydrogen and/or hydrocarbons in the presence of oxygen. If appropriate, a hydrocarbon-containing cofeed can additionally be mixed in.

The nonoxidative catalytic n-butane dehydrogenation can be carried out with or without an oxygen-containing gas as cofeed in a tray reactor. This comprises one or more successive catalyst beds. The number of catalyst beds can be from 1 to 20, advantageously from 1 to 6, preferably from 1 to 4 and in particular from 1 to 3. The reaction gas preferably flows radially or axially through the catalyst beds. In general, such a tray reactor is operated using one fixed bed of catalyst. In the simplest case, the fixed beds of catalyst are arranged axially or in the annular gaps between concentric cylindrical meshes in a shaft furnace reactor. One shaft furnace reactor corresponds to one tray. Carrying out the dehydrogenation in a single shaft furnace reactor corresponds to a preferred embodiment, with an oxygen-containing cofeed being able to be employed. In a further preferred embodiment, the dehydrogenation is carried out in a tray reactor having 3 catalyst beds. When the reactor is operated without an oxygen-containing gas as cofeed, the reaction gas mixture is subjected to intermediate heating in the tray reactor on its way from one catalyst bed to the next catalyst bed, e.g. by passing it over heat exchanger surfaces heated by means of hot gases or by passing it through tubes heated by means of hot combustion gases.

In a preferred embodiment of the process of the invention, the nonoxidative catalytic n-butane dehydrogenation is carried out autothermally. For this purpose, oxygen is additionally mixed into the reaction gas mixture of the n-butane dehydrogenation in at least one reaction zone and the hydrogen and/or hydrocarbon present in the reaction gas mixture is at least partly burnt to generate at least part of the required heat of dehydrogenation directly in the reaction gas mixture in the reaction zone or zones.

In general, the amount of oxygen-containing gas added to the reaction gas mixture is chosen so that the combustion of hydrogen present in the reaction gas mixture and, if appropriate, of hydrocarbons present in the reaction gas mixture and/or of carbon present in the form of carbon deposits generates the quantity of heat necessary for the dehydrogenation of the n-butane. In general, the total amount of oxygen introduced is, based on the total amount of butane, from 0.001 to 0.5 mol/mol, preferably from 0.005 to 0.2 mol/mol, particularly preferably from 0.05 to 0.2 mol/mol. Oxygen can be used either as pure oxygen or as oxygen-containing gas in admixture with inert gases, for example in the form of air. The inert gases and the resulting combustion gases generally have an additional diluting effect and thus promote the heterogeneously catalyzed dehydrogenation.

The hydrogen which is burnt to generate heat is the hydrogen formed in the catalytic n-butane dehydrogenation and also any hydrogen which is additionally added as hydrogen-containing gas to the reaction gas mixture. The amount of hydrogen present should preferably be such that the molar ratio of $H_2/O_2$ in the reaction gas mixture immediately after the introduction of oxygen is from 1 to 10 mol/mol, preferably from 2 to 5 mol/mol. In the case of multistage reactors, this applies to each intermediate introduction of oxygen-containing and, if applicable, hydrogen-containing gas.

The combustion of hydrogen occurs catalytically. The dehydrogenation catalyst used generally also catalyzes the combustion of hydrocarbons and of hydrogen in the presence of oxygen, so that a different, specific oxidation catalyst is in principle not necessary. In one embodiment, the dehydrogenation is carried out in the presence of one or more oxidation catalysts which selectively catalyze the combustion of hydrogen with oxygen in the presence of hydrocarbons. The combustion of these hydrocarbons in the presence of oxygen to form CO, $CO_2$ and water therefore proceeds to only a minor extent. The dehydrogenation catalyst and the oxidation catalyst are preferably present in different reaction zones.

When the reaction is carried out in a plurality of stages, the oxidation catalyst can be present in only one reaction zone, in a plurality of reaction zones or in all reaction zones.

The catalyst which selectively catalyzes the oxidation of hydrogen is preferably located at places where the prevailing oxygen partial pressures are higher than at other places in the reactor, in particular in the vicinity of the feed point for the oxygen-containing gas. Oxygen-containing gas and/or hydrogen-containing gas can be introduced at one or more points on the reactor.

In one embodiment of the process of the invention, oxygen-containing gas and hydrogen-containing gas are introduced intermediately upstream of each tray of a tray reactor. In a further embodiment of the process of the invention, oxygen-containing gas and hydrogen-containing gas are introduced upstream of each tray apart from the first tray. In one embodiment, a layer of a specific oxidation catalyst is present downstream of each point of introduction, followed by a layer of the dehydrogenation catalyst. In a further embodiment, no specific oxidation catalyst is present. The dehydrogenation temperature is generally from 400 to 1100° C., and the pressure in the last catalyst bed of the tray reactor is generally from 0.2 to 5 bar, preferably from 1 to 3 bar. The throughput (GHSV) is generally from 500 to 2000 h$^{-1}$, and in the case of high-load operation can also be up to 100 000 h$^{-1}$, preferably from 4000 to 16 000 h$^{-1}$.

A preferred catalyst which selectively catalyzes the combustion of hydrogen comprises oxides and/or phosphates selected from the group consisting of the oxides and phosphates of germanium, tin, lead, arsenic, antimony or bismuth. A further preferred catalyst which catalyzes the combustion of hydrogen comprises a noble metal of transition groups VIII and/or I.

The dehydrogenation catalysts used generally comprise a support and an active composition. The support generally comprises a thermally stable oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof as support. In the case of mixtures, these can be physical mixtures or chemical mixed phases such as magnesium-aluminum or zinc-aluminum mixed oxides. Preferred supports are zirconium dioxide and/or silicon dioxide, and particular preference is given to mixtures of zirconium dioxide and silicon dioxide.

The active composition of the dehydrogenation catalysts generally comprises one or more elements of transition group VIII, preferably platinum and/or palladium, particularly preferably platinum. In addition, the dehydrogenation catalysts can comprise one or more elements of main groups I and/or II, preferably potassium and/or cesium. Furthermore, the dehydrogenation catalysts can comprise one or more elements of transition group III including the lanthanides and actinides, preferably lanthanum and/or cerium. Finally, the dehydrogenation catalysts can comprise one or more elements of main groups III and/or IV, preferably one or more elements selected from the group consisting of boron, gallium, silicon, germanium, tin and lead, particularly preferably tin.

In a preferred embodiment, the dehydrogenation catalyst comprises at least one element of transition group VIII, at least one element of main groups I and/or II, at least one element of main groups III and/or IV and at least one element of transition group III including the lanthanides and actinides.

For example, all dehydrogenation catalysts disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 can be used according to the invention. Particularly preferred catalysts for the above-described variants of autothermal n-butane dehydrogenation are the catalysts described in examples 1, 2, 3 and 4 of DE-A 199 37 107.

The n-butane dehydrogenation is preferably carried out in the presence of water vapor. The added water vapor serves as heat carrier and aids the gasification of organic deposits on the catalysts, as a result of which the formation of carbon deposits on the catalysts is countered and the operating life of the catalysts is increased. The organic deposits are in this case converted into carbon monoxide, carbon dioxide and possibly water.

The dehydrogenation catalyst can be regenerated in a manner known per se. Thus, water vapor can be added to the reaction gas mixture or an oxygen-containing gas can be passed at elevated temperature over the catalyst bed from time to time so as to burn off the deposited carbon. The dilution with water vapor shifts the equilibrium in the direction of the products of the dehydrogenation. If appropriate, the catalyst is reduced by means of a hydrogen-containing gas after regeneration.

The n-butane dehydrogenation gives a gas mixture which comprises butadiene, 1-butene, 2-butene and unreacted n-butane together with secondary constituents. The usual secondary constituents are hydrogen, water vapor, nitrogen, CO and $CO_2$, methane, ethane, ethene, propane and propene. The composition of the gas mixture leaving the first dehydrogenation zone can vary widely depending on the way in which the dehydrogenation is carried out. Thus, when the preferred autothermal dehydrogenation with introduction of oxygen and additional hydrogen is carried out, the product gas mixture has a comparatively high content of water vapor and carbon oxides. In modes of operation without introduction of oxygen, the product gas mixture of the nonoxidative dehydrogenation has a comparatively high hydrogen content.

The product gas stream from the nonoxidative autothermal n-butane dehydrogenation typically comprises from 0.1 to 15% by volume of butadiene, from 1 to 15% by volume of 1-butene, from 1 to 25% by volume of 2-butene, from 20 to 70% by volume of n-butane, from 1 to 70% by volume of water vapor, from 0 to 10% by volume of low-boiling hydrocarbons (methane, ethane, ethene, propane and propene), from 0.1 to 40% by volume of hydrogen, from 0 to 70% by volume of nitrogen and from 0 to 5% by volume of carbon oxides.

In a part C of the process, the low-boiling secondary constituents other than the $C_4$-hydrocarbons (n-butane, isobutane, 1-butene, cis-/trans-2-butene, isobutene, butadiene) are at least partly but preferably essentially completely removed from the product gas stream from the n-butane dehydrogenation to give a $C_4$ product gas stream c.

The product gas stream b leaving the dehydrogenation zone is preferably divided into two substreams and only one of the two substreams is subjected to the further parts C to E of the process while the second substream is recirculated to the dehydrogenation zone. An appropriate mode of operation is described in DE-A 102 11 275. However, it is also possible for the entire product gas stream b from the n-butane dehydrogenation to be subjected to the further parts C to E of the process.

In one embodiment of the process of the invention, water is firstly separated off from the product gas stream b in part C of the process. The removal of water can, for example, be effected by condensation by cooling and/or compression of the product gas stream b and can be carried out in one or more cooling and/or compression stages. The water removal is usually carried out when the n-butane dehydrogenation is carried out autothermally or isothermally with introduction of water vapor (as in the Linde or STAR process for the dehydrogenation of propane) and the product gas stream b consequently has a high water content.

The low-boiling secondary constituents can be separated off from the product gas stream by conventional separation methods such as distillation, rectification, membrane processes, absorption or adsorption.

To separate off the hydrogen present in the product gas stream b from the n-butane dehydrogenation, the product gas mixture can, if appropriate after cooling, for example in an indirect heat exchanger, be passed over a membrane which is permeable only to molecular hydrogen and is generally configured as a tube. The molecular hydrogen which has been separated off in this way can if necessary be at least partly used in the dehydrogenation or else can be passed to another use, for example for the generation of electric energy in fuel cells.

The carbon dioxide present in the product gas stream b from the dehydrogenation can be removed by means of a $CO_2$ gas scrub. The carbon dioxide gas scrub can be preceded by a separate combustion stage in which carbon monoxide is selectively oxidized to carbon dioxide.

In a preferred embodiment of the process of the invention, the incondensable or low-boiling gas constituents such as hydrogen, carbon oxides, the low-boiling hydrocarbons (methane, ethane, ethene, propane, propene) and if applicable nitrogen are separated off in an absorption/desorption cycle using a high-boiling absorption medium to give a $C_4$ product gas stream c which consists essentially of the $C_4$-hydrocarbons. In general, the $C_4$ product gas stream c comprises at least 80% by volume, preferably at least 90% by volume, particularly preferably at least 95% by volume, of the $C_4$-hydrocarbons.

For this purpose, the product gas stream b is, if appropriate after prior water removal, brought into contact with an inert absorption medium in an absorption stage and the $C_4$-hydrocarbons are absorbed in the inert absorption medium, giving an absorption medium laden with $C_4$-hydrocarbons and an offgas containing the other gas constituents. In a desorption stage, the $C_4$-hydrocarbons are liberated again from the absorption medium.

Inert absorption media used in the absorption stage are generally high-boiling nonpolar solvents in which the $C_4$-hydrocarbon mixture to be separated off is significantly more soluble than are the remaining gas constituents to be removed. The absorption can be carried out by simply passing the product gas stream b through the absorption medium. However, it can also be carried out in columns or in rotary absorbers. It can be carried out in cocurrent, countercurrent or crosscurrent. Suitable absorption columns are, for example, tray columns having bubble cap trays, centrifugal trays and/or sieve trays, columns containing structured packing, e.g. sheet metal packing having a specific surface area of from 100 to 1000 $m^2/m^3$, e.g. Mellapak® 250 Y, and columns containing random packing. It is also possible to use trickle towers and spray towers, graphite block absorbers, surface absorbers such as thick film and thin film absorbers and also rotary columns, pan scrubbers, cross-spray scrubbers and rotary scrubbers.

Suitable absorption media are comparatively nonpolar organic solvents, for example, aliphatic $C_8$-$C_{18}$-alkenes or aromatic hydrocarbons such as middle oil fractions from paraffin distillation or ethers having bulky groups, or mixtures of these solvents, with a polar solvent such as 1,2-dimethyl phthalate being able to be added to these. Further suitable absorption media are esters of benzoic acid and phthalic acid with straight-chain $C_1$-$C_8$-alkanols, e.g. n-butyl benzoate, methyl benzoate, ethyl benzoate, dimethyl phthalate, diethyl phthalate, and also heat transfer oils such as biphenyl and diphenyl ether, their chlorinated derivatives and also triarylalkenes. One suitable absorption medium is a mixture of biphenyl and diphenyl ether, preferably a mixture having the azeotropic composition, for example the commercially available Diphyl®. This solvent mixture frequently contains from 0.1 to 25% by weight of dimethyl phthalate. Other suitable absorption media are octanes, nonanes, decanes, undecanes, dodecanes, tridecanes, tetradecanes, tetradecanes, pentadecanes, hexadecanes, heptadecanes and octadecanes and fractions which are obtained from refinery streams and comprise the linear alkanes mentioned as main components.

To desorb the $C_4$-hydrocarbons, the laden absorption medium is heated and/or depressurized to a lower pressure. As an alternative, the desorption can also be effected by stripping or in a combination of depressurization, heating and stripping in one or more process steps. The absorption medium which has been regenerated in the desorption stage is recirculated to the absorption stage.

In one process variant, the desorption step is carried out by depressurization and/or heating of the laden absorption medium.

The separation C is generally not absolutely complete, so that, depending on the way in which the separation is carried out, small amounts or even only traces of the further gas constituents, in particular the low-boiling hydrocarbons, can still be present in the $C_4$ product gas stream.

The $C_4$ product gas stream c obtained after removal of the secondary constituents consists essentially of n-butane, 1-butene, 2-butene and butadiene. In general, the stream c comprises from 10 to 80% by volume of n-butane, from 5 to 40% by volume of 1-butene, from 10 to 50% by volume of 2-butene and from 0 to 40% by volume of butadiene. The steam c preferably comprises from 15 to 65% by volume of n-butane, from 10 to 30% by volume of 1-butene, from 15 to 45% by volume of 2-butene and from 5 to 30% by volume of butadiene. In addition, the stream e can contain small amounts of further gas constituents such as isobutane, isobutene, $C_5^+$-hydrocarbons, propane and propene, generally in amounts of from 0 to 10% by volume, preferably from 0 to 5% by volume.

The volume flow minimization effected by the removal of the secondary constituents decreases the load on the subsequent stages of the process.

In a part D of the process, the $C_4$ product gas stream c consisting essentially of n-butane, 1-butene, 2-butene and butadiene is introduced into a selective hydrogenation zone and a selective hydrogenation of butadiene to 1-butene and/or 2-butene is carried out.

The selective hydrogenation can be carried out in a manner known per se in the gas phase, liquid phase or trickle phase. The selective hydrogenation is preferably carried out in the liquid phase or trickle phase using a fixed-bed hydrogenation catalyst. As hydrogenation catalysts, it is possible to use supported noble metal catalysts comprising palladium, platinum, silver, gold, rhodium, ruthenium, osmium or mixtures of these metals. Supported palladium-containing catalysts are particularly preferred as hydrogenation catalysts. A preferred hydrogenation catalyst used is described, for example, in EP-A 0 992 284. This comprises metals of groups 8, 9 and 10 of the Periodic Table, in particular ruthenium, rhodium, palladium and/or platinum, on an aluminum oxide support and, in addition, at least one metal of group 11 of the Periodic Table, preferably copper and/or silver. The amount of metal of group 8, 9 or 10 of the Periodic Table present in the catalyst is generally from 0.05 to 2% by weight, preferably from 0.1 to 0.5% by weight.

The selective hydrogenation can be carried out in one reactor or a plurality of reactors connected in series. The selective hydrogenation can, for example, be carried out in two stages. The temperature is usually in the range from 0° C. to 180° C. and the pressure is in the range from 2 to 50 bar. In one embodiment, the selective hydrogenation is carried out at a temperature of from 20 to 90° C. and a pressure in the range from 5 to 50 bar, with one mole of hydrogen being added per mole of butadiene.

The stream d leaving the selective hydrogenation zone consists essentially of n-butane, 1-butene and 2-butene. In general, the stream d comprises from 10 to 80% by volume of n-butane, from 10 to 60% by volume of 1-butene, from 15 to 60% by volume of 2-butene and from 0 to 5% by volume of butadiene. The stream d preferably comprises from 15 to 65% by volume of n-butane, from 15 to 45% by volume of 1-butene, from 20 to 50% by volume of 2-butene and from 0 to 1% by volume of butadiene. In addition, the stream d can contain small amounts of further gas constituents such as isobutane, isobutene, $C_5^+$-hydrocarbons, propane and propene, generally in amounts of from 0 to 10% by volume, preferably from 0 to 5% by volume.

In a part E of the process, the stream d is separated into a desired product stream e1 consisting essentially of 1-butene and a recycle stream e2 consisting essentially of 2-butene and n-butane.

The fractionation of the stream d consisting essentially of 1-butene, 2-butene and n-butane is generally carried out in a distillation column which generally has from 30 to 80 theoretical plates, preferably from 40 to 75 theoretical plates. Suitable columns are, for example, bubble cap tray columns, columns containing random or ordered packing or dividing wall columns. The reflux ratio is generally from 10 to 50. The distillation is generally carried out at a pressure of from 5 to 20 bar.

In the upper part of the column, preferably at the top of the column, the stream e1 consisting essentially of 1-butene is taken off. This generally comprises at least 90% by volume, preferably at least 95% by volume, of 1-butene and in addition up to 10% by volume, preferably up to 5% by volume, of further constituents such as n-butane and isobutene.

In the lower part of the column, preferably in the bottom fifth of the column, particularly preferably at a point from the bottom of the column up to at most 5 theoretical plates above the bottom of the column, a 2-butene-containing recycle stream e2 is taken off. This stream e2 usually comprises from 10 to 80% by volume of 2-butene and in addition from 20 to 90% by volume of n-butane and from 0 to 5% by volume of 1-butene. The stream e2 is, if appropriate after a purge gas stream has been separated off in order to avoid accumulation of high boilers, recirculated to the n-butane dehydrogenation.

EXAMPLE

A feed gas stream a of 140 946 t/a of n-butane is fed together with a recycle stream e2 consisting essentially of n-butane and 2-butene (234 276 t/a; n-butane 23.1%, cis-2-butene 40.5%, trans-2-butene 35.9%) into a dehydrogenation reactor and subjected to a nonoxidative catalytic dehydrogenation.

A product gas stream b having the following composition is obtained (all percentage figures below are % by mass): n-butane 15.9%, 1-butene 22.7%, cis-2-butene 18.9%, trans-2-butene 23.0%, butadiene 17.6%.

Hydrogen (8639 t/a) is separated off from the product gas stream b, and a selective hydrogenation is subsequently carried out with addition of hydrogen (2568 t/a).

A stream d (386 429 t/a) consisting essentially of n-butane, 1-butene and 2-butene and having the following composition is obtained: n-butane 16.1%, 1-butene 34.4%, cis-2-butene 26.2%, trans-2-butene 23.3%.

In the subsequent distillation, a desired product stream e1 (136 496 t/a) consisting essentially of 1-butene and a recycle stream e2 (234 276 t/a) consisting essentially of 2-butene and n-butane are obtained.

The desired product stream e1 has the following composition: n-butane 3.3%, 1-butene 96.6%, trans-2-butene 0.1%.

The recycle steam e2 has the composition indicated above.

The invention claimed is:

1. A process for preparing 1-butene from 1-butane, which comprises the steps
    A) provision of an n-butane-containing feed gas stream a;
    B) introducing of the n-butane-containing feed gas stream a into at least one dehydrogenation zone and nonoxidative catalytic dehydrogenation of n-butane to give a product gas stream b comprising n-butane, 1-butene, 2-butene, butadiene, low-boiling secondary constituents, hydrogen and possibly water vapor;
    C) removing hydrogen, the low-boiling secondary constituents and optionally water vapor to give a $C_4$ product gas stream c containing 10-80% by volume of n-butane, 5-40% by volume of 1-butene, 10-50% by volume of 2-butene, 0-40% by volume of butadiene and 0-10% by volume of further gas constituents;
    D) introducing the $C_4$ product gas stream c, containing 10-80% by volume of n-butane, 10-60% by volume of 1-butene, 15-60% by volume of 2-butene, 0-5% by volume of butadiene and 0-10% by volume of further gas constituents, into a selective hydrogenation zone and selective hydrogenation of butadiene to 1- and/or 2-butene to give a stream d consisting essentially of n-butane, 1-butene and 2-butene;
    E) separating of the stream d by distillation into a desired product stream e1 consisting essentially of 1-butene and a recycle stream e2 consisting essentially of 2-butene and n-butane and recirculation of the recycle stream e2 consisting essentially of 2-butene and n-butane to the dehydrogenation zone, wherein the stream e1 contains at least 90% by volume of 1-butene, and the stream e2 contains 10-80% by volume of 2-butene, 20-90% by volume of n-butane and 0-5% by volume of 1-butene.

2. A process according to claim 1, wherein the dehydrogenation of n-butane is carried out as an autothermal dehydrogenation.

3. A process according to claim 1, wherein the removal of the low-boiling secondary constituents is carried out by means of a high-boiling solvent in an absorption/desorption cycle.

4. The process as claimed in claim 1, wherein oxygen is additionally mixed into the reaction gas mixture of the n-butane dehydrogenation in at least one reaction zone and the hydrogen and/or hydrocarbon present in the reaction gas mixture is at least partly burnt to generate at least part of the required heat of dehydrogenation directly in the reaction gas mixture in the reaction zone or zones.

5. The process as claimed in claim 4, wherein the total amount of oxygen introduced is, based on the total amount of butane, from 0.001 to 0.5 mol/mol.

6. The process as claimed in claim 4, wherein the total amount of oxygen introduced is, based on the total amount of butane, from 0.005 to 0.2 mol/mol.

7. The process as claimed in claim 4, wherein the total amount of oxygen introduced is, based on the total amount of butane, from 0.05 to 0.2 mol/mol.

8. The process as claimed in claim 4, wherein the oxygen is pure oxygen or as oxygen-containing gas.

9. The process as claimed in claim 4, wherein the oxygen-containing gas is air.

10. The process as claimed in claim 1, wherein stream c comprises from 15 to 65% by volume of n-butane, from 10 to 30% by volume of 1-butene, from 15 to 45% by volume of 2-butene and from 5 to 30% by volume of butadiene.

11. The process as claimed in claim 1, wherein stream d comprises from 15 to 65% by volume of n-butane, from 15 to 45% by volume of 1-butene, from 20 to 50% by volume of 2-butene, from 0 to 1% by volume of butadiene and 0 to 5% by volume of further gas constituents.

12. The process as claimed in claim 10, wherein stream d comprises from 15 to 65% by volume of n-butane, from 15 to 45% by volume of 1-butene, from 20 to 50% by volume of 2-butene, from 0 to 1% by volume of butadiene and 0 to 5% by volume of further gas constituents.

* * * * *